US00PP16680P2

(12) United States Plant Patent
de Jong

(10) Patent No.: US PP16,680 P2
(45) Date of Patent: Jun. 20, 2006

(54) ***RUSCUS* PLANT NAMED 'CHRISTMAS BERRY'**

(50) Latin Name: *Ruscus aculeatus*
Varietal Denomination: Christmas Berry

(76) Inventor: Gys Petrus de Jong, Marian Nurseries, Newhaggart, Lusk, Co. Dublin (IE)

( * ) Notice: Subject to any disclaimer, the term of this patent is extended or adjusted under 35 U.S.C. 154(b) by 61 days.

(21) Appl. No.: 11/045,978

(22) Filed: Jan. 28, 2005

(51) Int. Cl.
*A01H 5/00* (2006.01)

(52) U.S. Cl. ..... Plt./226

(58) Field of Classification Search ..... Plt./263, Plt./226

See application file for complete search history.

*Primary Examiner*—Kent Bell
*Assistant Examiner*—W. C. Haas
(74) *Attorney, Agent, or Firm*—C. A. Whealy

(57) ABSTRACT

A new and distinct cultivar of *Ruscus* plant named 'Christmas Berry', characterized by its upright plant habit; glossy green-colored cladophylls; numerous glossy and bright red-colored fruits; and good garden performance.

2 Drawing Sheets

Botanical designation: *Ruscus aculeatus.*
Cultivar denomination: 'Christmas Berry'.

BACKGROUND OF THE INVENTION

The present Invention relates to a new and distinct cultivar of *Ruscus* plant, botanically known as *Ruscus aculeatus,* and hereinafter referred to by the name 'Christmas Berry'.

The new cultivar is a chance seedling from an open-pollination of unknown selections of *Ruscus aculeatus.* The new *Ruscus* was discovered and selected as a single plant by the Inventor on Aug. 10, 2003 in a controlled environment in North Co., Dublin, Ireland.

Asexual reproduction of the new *Ruscus* by divisions since Aug. 10, 2003 in North Co., Dublin, Ireland, has shown that the unique features of this new *Ruscus* are stable and reproduced true to type in successive generations of asexual reproduction.

SUMMARY OF THE INVENTION

The following traits have been repeatedly observed and are determined to be the unique characteristics of 'Christmas Berry'. These characteristics in combination distinguish 'Christmas Berry' as a new and distinct cultivar:

1. Upright plant habit.
2. Glossy green-colored cladophylls.
3. Numerous glossy and bright red-colored fruits.
4. Good garden performance.

Plants of the new *Ruscus* can be compared to plants of the *Ruscus* cultivar Sparkler, not patented. In side-by-side comparisons conducted in North Co., Dublin, Ireland, plants of the new *Ruscus* differed from plants of the cultivar Sparkler in the following characteristics:

1. Plants of the new *Ruscus* were more vigorous and denser than plants of the cultivar Sparkler.
2. Plants of the new *Ruscus* had shinier, brighter and darker green-colored leaves than plants of the cultivar Sparkler.
3. Plants of the new *Ruscus* had more berries per cladophyll than plants of the cultivar Sparkler.

4. Plants of the new *Ruscus* and the cultivar Sparkler differed in fruit color as plants of the cultivar Sparkler had purple-colored fruits.

Plants of the new *Ruscus* can also be compared to plants of the *Ruscus* cultivar John Redmond, not patented. In side-by-side comparisons conducted in North Co., Dublin, Ireland, plants of the new *Ruscus* differed from plants of the cultivar John Redmond in the following characteristics:

1. Plants of the new *Ruscus* were more vigorous and denser than plants of the cultivar John Redmond.
2. Plants of the new *Ruscus* had shinier, brighter and darker green-colored leaves than plants of the cultivar John Redmond.
3. Plants of the new *Ruscus* had more berries per cladophyll than plants of the cultivar John Redmond.
4. Plants of the new *Ruscus* and the cultivar John Redmond differed in fruit color as plants of the cultivar John Redmond had dark red-colored fruits.

BRIEF DESCRIPTION OF THE PHOTOGRAPHS

The accompanying colored photographs illustrate the overall appearance of the new *Ruscus,* showing the colors as true as it is reasonably possibly to obtain in colored reproductions of this type. Colors in the photographs may differ slightly from the color values cited in the detailed botanical description which accurately describe the colors of the new *Ruscus.*

The photograph on the first sheet comprises a side perspective view of a typical plant of 'Christmas Berry' grown in a container.

The photograph at the top of the second sheet is a close-up view of typical fruits of 'Christmas Berry'.

The photograph at the bottom of the second sheet is a close-up view of a typical flowers and leaves of 'Christmas Berry'.

DETAILED BOTANICAL DESCRIPTION

The new *Ruscus* has not been observed under all possible environmental conditions. The phenotype may vary somewhat with variations in environment such as temperature and light intensity, without, however, any variance in genotype.

The aforementioned photographs, following observations and measurements describe plants grown in 2-liter containers in Boskoop, The Netherlands, in an outdoor nursery and under commercial production practices. Plants used for the photographs and the description were about two years old. The photographs and description were taken during the fall with day temperatures ranging from 7° to 15° C. and night temperatures ranging from −4° C. to 8° C. In the following description, color references are made to The Royal Horticultural Society Colour Chart, 2001 Edition, except where general terms of ordinary dictionary significance are used.

Botanical classification: *Ruscus aculeatus* cultivar Christmas Berry.

Parentage: Chance seedling from an open-pollination of unknown selections of *Ruscus aculeatus*.

Propagation:

*Type.*—By divisions.

*Time to produce a rooted young plant.*—About eight months.

*Root description.*—Thick, fleshy; white in color.

*Rooting habit.*—Freely branching; dense.

Plant description:

*Plant form.*—Upright perennial evergreen shrub.

*Growth habit.*—Moderate to low vigor. Freely basal branching; about ten stems per plant; dense and bushy growth habit.

*Plant height.*—About 25 cm.

*Plant width (spread).*—About 20.5 cm.

*Stem description.*—Length: About 17.5 cm. Diameter: About 4 mm. Internode length: About 3.5 mm. Strength: Strong. Texture: Smooth; glabrous. Color: 137A.

*Cladophyll description.*—Arrangement: Alternate; simple; sessile. Length: About 2 cm. Width: About 1 cm. Shape: Elliptic to broadly ovate. Apex: Sharp mucronate. Base: Cuneate. Margin: Entire. Texture, upper and lower surfaces: Smooth, glabrous; leathery; glossy. Color: Developing cladophylls, upper and lower surfaces: 146A to 146B. Fully expanded cladophylls, upper and lower surfaces: 137A to 137B; venation, 137A to 137B.

Flower description:

*Flower type and habit.*—Inconspicuous single rotate flowers; situated on top of the cladophylls. Flowers not fragrant. Freely flowering, about 18 flowers per stem. Flowers not persistent. Flowers face mostly upright, about 45° from vertical.

*Natural flowering season.*—Continuous flowering; typically midsummer into the fall in The Netherlands.

*Longevity.*—Flowers last about one week on the plant.

*Flower buds.*—Height: About 2 mm. Diameter: About 2 mm. Shape: Globular. Color: 144C.

*Flowers.*—Diameter: About 2 mm. Depth: About 2 mm.

*Inner perianth segments.*—Quantity per flower: Three. Length: About 1.5 mm. Width: About 0.8 mm. Shape: Ovate. Apex: Acute. Base: Attenuate. Margin: Entire. Texture, upper and lower surfaces: Smooth; glabrous. Color: Developing and fully expanded inner perianth segments, upper surface: 144B to 144C; towards the base, between 86A and N187A. Developing and fully expanded inner perianth segments, lower surface: 144B to 144C; towards the base, between 86A and N187A.

*Outer perianth segments.*—Quantity per flower: Three. Length: About 2.5 mm. Width: About 2 mm. Shape: Broadly ovate. Apex: Broadly acute. Base: Cuneate. Margin: Entire. Texture, upper and lower surfaces: Smooth; glabrous. Color: Developing and fully expanded outer perianth segments, upper surface: 144A to 144B. Developing and fully expanded outer perianth segments, lower surface: 144A to 144B.

*Peduncles.*—Length: About 2 mm. Diameter: About 0.5 mm. Orientation: Erect to about 5° from axis of cladophyll. Strength: Weak to moderately strong. Texture: Smooth, glabrous. Color: 144B.

*Reproductive organs.*—Stamens: Quantity per flower: About three. Anther shape: Reniform. Anther length: About 0.3 mm. Anther color: 145C to 145D. Pollen amount: Abundant. Pollen color: 145D. Pistils: Quantity per flower: One. Pistil length: About 0.3 mm. Stigma shape: Capitate. Stigma color: N186A. Style length: About 0.3 mm. Ovary color: N186A.

*Fruits.*—Quantity per flower: One. Days to ripening: About two months. Type: Berry. Shape: Roughly spherical. Length: About 1 cm. Diameter: About 1.3 cm. Texture: Smooth; glabrous; glossy. Color: Immature: 141B. Developing: N30A. Fully developed: 45A to 46B.

*Seeds.*—Quantity per fruit: About two. Length: About 6 mm. Diameter: About 8 mm. Texture: Smooth; glabrous. Color: 165B.

Disease/pest resistance: Plants of the new *Ruscus* have not been observed to be resistant pathogens or pests common to *Ruscus*.

Garden performance: Plants of the new *Ruscus* have been observed to have good garden performance and tolerate rain wind and temperatures ranging from −20° C. to 40° C.

It is claimed:

1. A new and distinct cultivar of *Ruscus* plant named 'Christmas Berry', as illustrated and described.

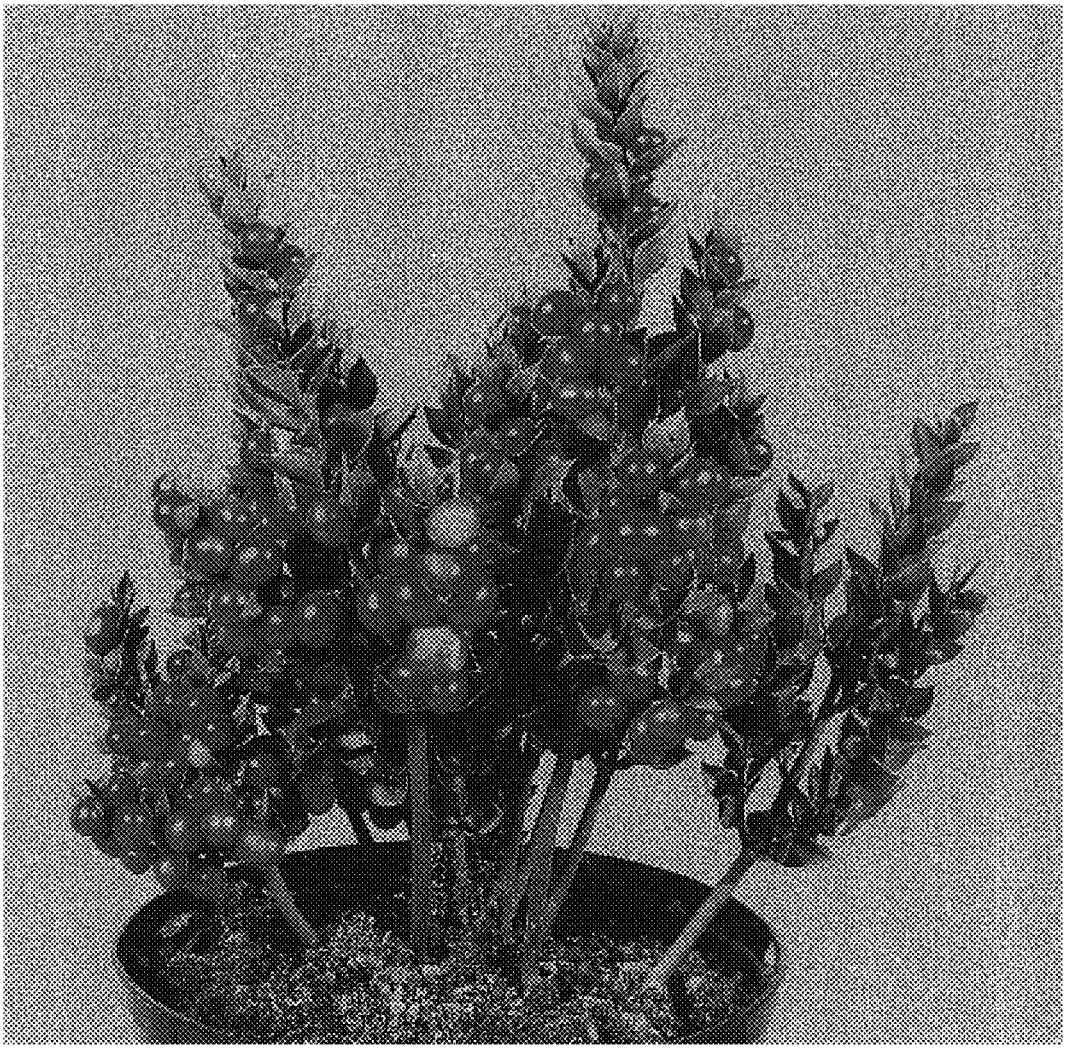

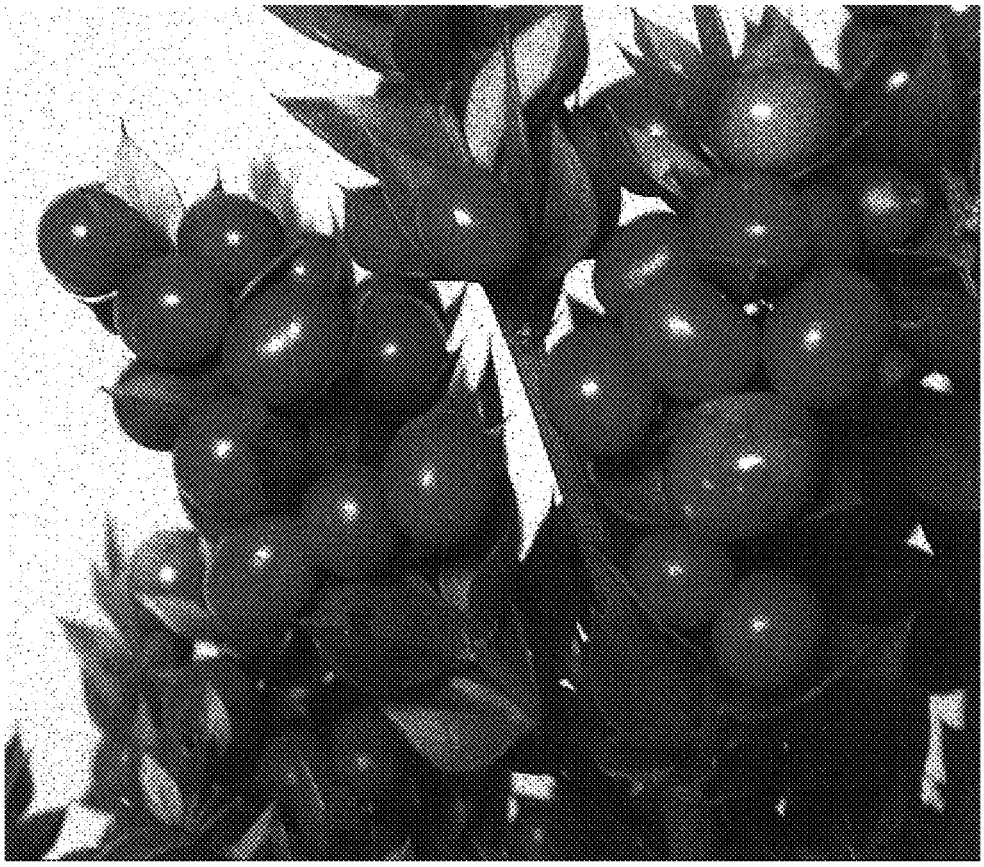
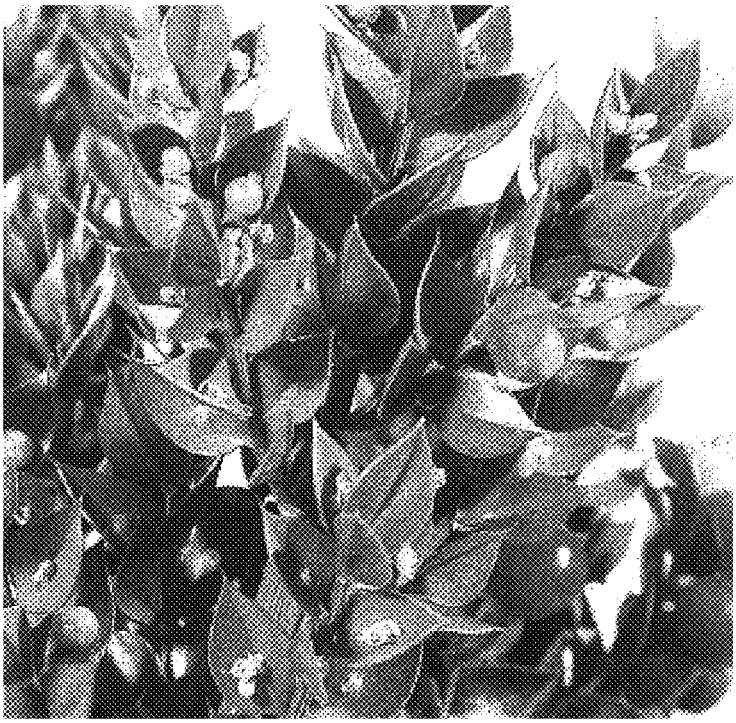

* * * * *